United States Patent [19]

Irie

[11] Patent Number: 5,208,146
[45] Date of Patent: May 4, 1993

[54] MURINE MONOCLONAL ANTI-IDIOTYPE ANTIBODIES

[75] Inventor: Reiko F. Irie, Los Angeles, Calif.

[73] Assignee: The Regents of the University of California, Oakland, Calif.

[21] Appl. No.: 609,255

[22] Filed: Nov. 5, 1990

[51] Int. Cl.$^5$ .................. G01N 33/536; C12N 5/20; A61K 35/14; C07K 15/28

[52] U.S. Cl. ........................ 435/7.23; 435/240.27; 435/7.92; 530/387.2; 530/809; 424/85.8

[58] Field of Search ............... 424/85.8; 530/387.2, 530/387.1, 809; 435/240.27, 7.23, 7.92

[56] References Cited

U.S. PATENT DOCUMENTS

| | | | |
|---|---|---|---|
| 4,557,931 | 12/1985 | Irie et al. | 424/88 |
| 4,918,164 | 4/1990 | Hellstrom et al. | 530/387 |
| 5,053,224 | 10/1991 | Koprowski et al. | 424/85.8 |

OTHER PUBLICATIONS

Irie, et al. "Human antibody to OFA-I, a tumor antigen, produced in vitro by Epstein-Barr virus-transformed human B-lymphoid cell lines", Proceedings National Academy of Sciences, vol. 79, pp. 5666-5670, Sep., 1982.

Cahan, et al., "Identification of a human neuroectodermal tumor antigen (OFA-1-2) as ganglioside GD2," Proceedings National Academy of Sciences, vol. 79, pp. 7629-7633, Dec., 1982.

Raychaudhuri, et al., "Potential role of antiidiotype antibodies in active tumor immunotherapy," Critical Review in Oncology/Hematology, vol. 9, issue 2, 1989.

Nepom, et al., "Induction of immunity to a human tumor by in vivo administration of antiidiotype antibodies in mice," Proceedings National Academy of Sciences, vol. 81, pp. 2864-2867, May, 1984.

Dagleish, et al., "Antiidiotypic antibodies as immunogens: idiotype-based vaccines," Vaccine, vol. 6, pp. 215-220, Jun., 1988.

Tai, et al., "Ganglioside GM2 as a human tumor antigen (OFA-I-1)", Proceedings of the National Academy of Sciences, vol. 80, pp. 5392-5396, Sep., 1983.

Kusama, et al., "Syngeneic antiidiotypic antisera to murine antihuman high-molecular weight melanoma-associated antigen monoclonal antibodies," Cancer Research, vol. 47, pp. 4312-4317, Aug., 1987.

Jerne, N. K. Towards a network theory of the immune system. Ann Immunol (Paris) 125C:373-389, 19794.

Sikorska, H. M. Therapeutic applications of anti-idiotypic antibodies. J Biol Res Mod 7:327-358, 1988.

Livingston, P. O., Natoli, E. J., Calves, M. J., Stockert, E., Oettgen, H.F., Old, L. J. Vaccines containing purified GM2 ganglioside elicit GM2 antibodies in melanoma patients. Proc Natl Acad Sci USA 84:2911-2915, 1987.

Livingston, P. O. Experimental and clinical studies with active specific immunotherapy. In "Immunity to Cancer II" Eds M. S. Mitchell, Pub Alan L. Liss, Inc, N.Y. pp. 309-321 (1989).

Herlyn, D. Wettendorff, M. Schmoll, E. Anti-idiotype immunization of cancer patients: modulation of immune response. Proc Natl Acad Sci 84:8055-8059, 1987.

Bhattacharya-Chatterjee, M., Pride, M. W., Seon, B. K., Kohler, H. Idiotype vaccines against human T-cell acute lymphoblastic leukemia. I. Generation and characterization of biologically active monoclonal anti-idiotypes. J. Immunol 139:1354-1360, 1987.

(List continued on next page.)

Primary Examiner—Y. Christina Chan
Attorney, Agent, or Firm—Poms, Smith, Lande & Rose

[57] ABSTRACT

Murine monoclonal anti-idiotype antibodies raised against a human monoclonal anti-ganglioside antibody identified as L612. Both alpha and beta type anti-idiotype antibodies are disclosed which belong to the IgG1 class and contain kappa light chains. Two hybridoma cell lines which produced the monoclonal anti-idiotype antibodies are identified. The beta-type anti-idiotype antibodies are useful as an immunization agent to raise antibodies which are immunoreactive with tumors. The alpha-type anti-idiotype antibodies are useful as a probe for use in detecting human monoclonal antibodies bound to biopsied tumor tissues and to identify expression of ganglioside antigens on biopsied human tissues.

3 Claims, No Drawings

OTHER PUBLICATIONS

Viale, G., Grassi, F., Pelagi, M., Alzani, R., Menard, S., Miotti, S., Buffa, R., Gina, A., Siccardi, A. G. Anti-human tumor antibodies induced in mice and rabbits by "internal image" anti-idiotype monoclonal immunoglobulins. J Immunol 139:4250–4255, 1987.

Chen, H., Mittelman, A., Yamada, M. Association of restricted specificity of anti-anti-idiotypic antibodies with prolonged survival of melanoma patients. Proc Amer Assoc Clin Oncol 8:A1125, 1989.

Kahn, M., Hellstrom, I., Estin, C. D., Hellstrom, K. E., Monoclonal anti-idiotypic antibodies related to the p97 melanoma antigen. Cancer Res 49:3157–3162, 1989.

Irie, R. F., Matsuki, T., Morton, D. L. Human monoclonal antibody to ganglioside GM2 for melanoma treatment. Lancet 1:786–787, 1989.

Tsuchida, T., Saxton, R. E., Morton, D. L., Irie, R. F. Gangliosides of human melanoma II. Cancer, 623:1166–1174, 1989.

Ravindranath, M. H., Morton, D. L., Irie, R. F. An epitope common to ganglioside O-acetyl AD3 recognized by antibodies in melanoma patients after active specific immunotherapy. Cancer Res 49:3891–3897, 1989.

Hoon, D. B. S., Ando, I., Sviland, G., Tsuchida, T., Okun, E., Morton, D. L., Irie, R. F. Ganglioside GM2 expression on human melanoma cells correlates with sensitivity to lymphokine-activated killer cells. Int J Cancer 43:857–862, 1989.

Hoon, D. B. S., Irie, R. F., Cochran, A. J. Gangliosides from human melanoma immodulate response of T-cells to interleukin-2. Cell Immunol 111:410–419, 1988.

Ravindranath, M. H., Paulson, J. C., Irie, R. F. Human melanoma antigen O-acetylated ganglioside GD3 is recognized by cancer autennarius lectin.1 J Biol Chem 263:2079–2086, 1988.

Tsuchida, T., Ravindranath, M. H., Saxton, R. E., Irie, R. F. Gangliosides of human melanoma: Altered expression in vivo and in vitro. Cancer Res 47:1278–1281, 1987.

Tai, T., Sze, L. L., Kawashima, I., Saxton, R. E., Irie, R. F. Monoclonal antibody detects monosialoganglioside having sialic acid 2-3 Galactosyl residue. J Biol Chem 262:6803–6807, 1987.

Ando, I., Hoon, D. S. B., Suzuki, Y., Saxton, R. E., Golub, S. H., Irie, R. F. Ganglioside GM2 on the K56 cell line is recognized as a target structure by human natural killer cells. Int J Cancer 40:12–17, 1987.

Tsuchida T., Saxton, R. E., Irie, R. F. Gangliosides of human melanoma: GM2 and tumorigenicity. J Natl Cancer Inst 78:55–60, 1987.

Tsuchida, T., Saxton, R. E., Morton, D. L., Irie, R. F. Gangliosides of human melanoma. J Natl Cancer Inst 78:45–54, 1987.

Irie, R. F., Morton, D. L. Regression of cutaneous metastatic melanoma by intralesional injection with human monoclonal antibody to ganglioside GD2. Proc Natl Acad Sci 83:8694–8698, 1986.

Katano, M., Irie, R. F. Suppressed growth of human melanoma in nude mice by human monoclonal antibody to ganglioside GD2. Immunology Letters 8:169–174, 1984.

Katano, M., Saxton, R. E., Irie, R. F. Human monoclonal antibody to tumor-associated ganglioside GD2. J Clin Lab Immunol 15:119–126, 1984.

Tai, T., Cahan, L. D., Tsuchida, T., Saxton, R. E., Irie, R. F., Morton, D. L. Immunogenicity of melanoma-associated gangliosides in cancer patients. Int J Cancer 35:607–612, 1985.

Yano, T., Yasumoto, K., Nagashima, A., Murakami, H., Hashizume, S, and Nomoto, K. (1988) Immunohistological characterization of human monoclonal antibody against lung cancer. J Surg Oncol. 39, 108–113 (1988).

MURINE MONOCLONAL ANTI-IDIOTYPE ANTIBODIES

This invention was made with Government support under Grant Nos. CA 30647, CA 42396 and CA 12582 awarded by the National Cancer Institute.

BACKGROUND OF THE INVENTION

1. Field of the Invention

The present invention relates generally to anti-idiotype monoclonal antibodies and their use as surrogate antigens, immunomodulators, immunosuppressants and immunodiagnostic agents More particularly, the present invention involves murine monoclonal anti-idiotype antibodies which are developed against a human monoclonal antibody reactive to cancer cells. The present invention not only involves use of the anti-idiotype antibodies, but also includes the cell line which produce the anti-idiotype antibodies.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

The possibility that the variable regions of immunoglobulins could act as external antigens was first recognized by Jerne in his idiotype network theory (1). According to this theory, recognition of idiotypes on the antigen-combining site, or on the framework of AB1, results in the production of anti-idiotypes (anti-ids or AB2) beta and alpha, respectively. Such "internal image" anti-idiotypes, by virtue of their complementarity with the original antigen binding site, mimic the original antigen and often behave in a similar biological manner. The concept of internal image refers to the fact that some AB2 molecules can act as surrogate antigens and their administration can lead to the production of anti-anti-idiotype antibodies displaying similar characteristics of AB1.

Immunization using anti-ids as surrogate antigens has generated much interest among researchers, many of whom have experimented with AB2 vaccines for active specific immunization against viruses, bacteria, and other pathogens (2,3). This approach is useful when a conventional vaccine or antibodies are not available, or are difficult to produce or when the corresponding antigen is not a suitable product for genetic engineering. In addition, anti-ids can be used as immunomodulators for up-regulating immunity against cancer, and as immunosuppressants to prevent rejection of transplanted organs and to prevent the progression of auto-immune disease.

Gangliosides are glycospingolipids that are fundamental membrane components on human tissues. Gangliosides undergo characteristic changes during malignant transformation of normal cells and thus are desirable target antigens for immunotherapy of cancer. Melanoma synthesizes a large number of gangliosides and thus has served as a useful model to assess the potential of gangliosides as immunotherapy targets. A number of tumor-associated gangliosoides of human melanoma and their respective immonogenicity have been defined (12-29). In addition, it has been shown that active immunization with ganglioside antigens results in prolonged survival of melanoma patients (4,5). Nevertheless, this technique suffers in many areas, namely that the ganglioside antigen are many times rare or in short supply.

Tumor-associated antigens, in most cases, are present in nature only at low levels and are relatively difficult to purify in large amounts. In contrast, anti-ids can be secreted from hybridoma cells at low cost over long periods of time. Furthermore, current genetic engineering technology, while not applicable to ganglioside epitopes, can be used to synthesize the anti-id peptides. Anti-ids previously developed for active specific immunotherapy of human cancer have used murine monoclonal antibodies (MuMabs) as the immunogens (6-11).

In addition to their use as surrogate antigens, murine monoclonal antibodies have also been employed to define and characterize many antigenic molecules on human cancer cells. Murine monoclonal antibodies have several advantages over human monoclonal antibodies including a strong affinity for tumor antigens, higher antibody secretion by hybridoma ascites, and high antigen density on tumor cells. However, with respect to therapeutic use, recent clinical trials with murine monoclonals have indicated that human monoclonal antibodies (HuMAbs) may be preferable since repeated injections of MuMAbs induce anti-murine Ig antibodies in virtually all patients. This leads to formation of immune complexes and immune reactions with potentially hazardous complications. In addition, HuMAbs may recognize epitopes that are overlooked by the murine immune system.

The development of HuMAbs that react with ganglioside antigens on human cancer cells and the demonstration of their anti-tumor effect at the clinical level has been reported (23,12). Patients with recurrent melanoma received intratumor injections of HuMAb to ganglioside GD2 or GM2, and partial or complete regression was observed in about 70% of the patients. In those melanoma patients in whom the immunotherapy was ineffective, the target antigen GD2 or GM2, was not expressed on the tumor cells.

Because the quantity and quality of gangliosides on human melanoma are widely heterogeneous between different cancer patients, it is desireable to avoid unnecessary administration of HuMAb by examination of a pre-treatment biopsy to identify which gangliosides dominate on each patient's tumor cells.

There are three different immunological assays which have been used to detect the quality and quantity of gangliosides present on a given tumor. They include: the immune adherence assay (IA); direct immunofluoresence with fluorescinated microspheres; and IA absorption, and a biochemical assay. These assays each have certain limitations and advantages. The immunologic assay requires single cell suspensions from the biopsied tumor tissues. However, it is often difficult to obtain viable high yield tumor cell populations. Also, under a light microscope, tumor cells may not be readily distinguished from monocytes and macrophages. The biochemical assay does not require intact cells. However, a relatively large volume of tumor is necessary for ganglioside extraction and measurement of sialic acid in the glycolipid preparation.

The most commonly utilized immunologic technique for defining antigen expression on biopsy specimens using murine monoclonal antibodies is immunohistochemical staining of tissue sections. However, this sensitive method is not readily applicable to combinations of human monoclonal antibodies and human tissues. The indirect staining of human tumor tissues with the second antibody (anti-human Ig) usually results in high background from non-specific binding to abundant endogenous human Ig. Direct immunostaining using biotinylated human monoclonal antibodies may overcome this high background (30). However, this method is usually less sensitive and is most effective when a high density antigen is present on the cell surface.

As is apparent from the above background, there presently is a need to provide additional types of anti-idiotype antibodies which can be used as surrogate antigens in treating tumors. There also is a need to provide an improved method for detecting the presence of specific antigens on human tumor tissue to aid in selecting which anti-ids, or other monoclonal antibodies are to be used in treatment.

SUMMARY OF THE INVENTION

In accordance with the present invention, a new group of murine monoclonal anti-idiotype antibodies has been discovered which mimics the sialic acid-galactose residue of tumor gangliosides. It was discovered that the beta-type anti-ids in accordance with the present invention are useful as a surrogate antigen for use in treating cancers such as melanoma. It was further discovered that the alpha-type anti-ids in accordance with the present invention are useful in immunohistochemical staining procedures to provide sensitive and specific detection of gangliosides present on tumor cells.

The anti-idiotype antibodies in accordance with the present invention are raised against a human monoclonal anti-ganglioside antibody which is identified as L612. The L612 antibody is produced by a B-lymphoblastoid cell line which is maintained at the Division of Surgical Oncology at the University of California at Los Angeles School of Medicine.

The anti-idiotype antibodies in accordance with the present invention may be either an alpha-type or a beta-type. Both types are produced in relatively large quantities by hybridoma cell lines. As a feature of the present invention, a particularly suitable hybridoma cell line identified as 4C10 has been developed for producing beta-type anti-ids in accordance with the present invention. The 4C10 hybridoma cell line is maintained at the division of Surgical Oncology at the University of California at Los Angeles School of Medicine and has been deposited at the American Type Culture Collection under ATCC assession number HB10722 on Apr. 4, 1991 (12301 Parklawn Drive, Rockville, Md. 20852). The beta-type monoclonal anti-id produced by the 4C10 hybridoma is expected to be useful in treating melanoma tumors.

As another feature of the present invention, a second hybridoma cell line has been isolated which is particularly well-suited for producing alpha-type monoclonal anti-ids in accordance with the present invention. This hybridoma cell line has been identified as 18C6 and is also presently maintained at the Division of Surgical Oncology at the University of California at Los Angeles School of Medicine. The 18C6 hybridoma cell line has been deposited at the American Type Culture Collection under ATCC assession number HB10723 on Apr. 4, 1991. The alpha-type anti-id produced by the 18C6 hybridoma cell line has been found to be useful in improving the specificity of immunohistochemical staining of tissue sections to determine which gangliosides are present on tumor cells.

The above-described features along with many other features and attendant advantages of the present invention will become apparent as the invention becomes better understood by reference to the following detailed description.

DETAILED DESCRIPTION OF THE INVENTION

The anti-idiotype antibodies (anti-ids) in accordance with the present invention are mouse IgG(Kappa) monoclonal antibodies which are raised to the monoclonal antibody identified as L612 which is secreted by the human B-cell line that is also identified as L612 and which is maintained at the Division of Surgical Oncology at the University of California at Los Angeles School of Medicine. The L612 cell line has been deposited at the American Type Culture, Collection under ATCC accession number CRL10724 on Apr. 4, 1991.

The L612 cell line was established in culture from lymphocytes by the Epstein-Barr virus transformation technique used to produce two other human monoclonal anti-ganglioside antibodies, L55 (anti-GM2) and L72 (anti-GD2) (26–27). The L612 monoclonal antibody reacts strongly with human melanoma tumor biopsies. The L612 antibody also reacts less strongly with human tumor biopsies from lung cancer, breast cancer, pancreatic cancer, colon cancer and kidney cancer. The UCLASO-M12 melanoma cell line was identified as the most reactive cell line among the lines tested with the L612 monoclonal antibody. The UCLASO-M12 cell line is maintained at the Division of Surgical Oncology at the University of California at Los Angeles School of Medicine.

The L612 cell line was initially grown in RPMI 1640 medium containing fetal bovine serum, but later was adapted to a serum free medium containing a growth factor (SGF-6S) in CEM 2000 from Scott Laboratories, (Carson, Calif.); or AIM medium from Gibco Laboratories, (Grand Island, N.Y.). Human IgM in the spent medium was purified as previously described (25).

The anti-ids in accordance with the present invention are produced by hybridomas which are prepared according to the following exemplary procedure:

BALB/c mice were immunized by a subcutaneous injection of 200 ug of purified L612 monoclonal antibody in complete Freund's adjuvant. After 2 weeks the animals were boosted by another subcutaneous injection of L612 in incomplete Freund's adjuvant. Eleven days following the booster, the mice were injected intraperitoneally with 200 ug of L612 in saline. After three days the spleens were removed and the splenocytes fused with myeloma cell line SP2/0 using the standard procedure to produce hybridomas.

After HAT medium selection, hybridoma culture wells were tested for antibody using ELISA. Hybridomas secreting anti-ids (AB2) were identified by their strong binding reactivity to HuMAb L612 and absent reactivity to three other control human IgMs: L55, L72, and human serum IgM. Unrelated proteins used as antigens included fetal bovine serum and human serum albumin. 50 ul of IgMs or proteins (50 ug/ml) were coated on a 96-well ELISA plate and served as antigens to detect AB2. Peroxidase-conjugated goat anti-mouse IgG+IgM was used as the AB2 detection probe followed by substrate and reading absorbancy at 490 nm as described previously (19).

HAT selection of approximately 2500 hybridoma culture wells which were prepared as described above yielded 40 hybridomas secreting antibodies with distinct reactivity to L612 HuMAb, but no reactivity to three other control human IgMs and two unrelated serum protein antigens. To determine whether these anti-L612 antibodies were AB2 beta-type directed against the antigen combining site of L612, or were AB2 alpha antibodies bound to peptide regions outside the antigen-combining site of L612, the inhibitory activity of these anti-L612 antibodies against L612 binding to GM3 positive target cell lines or to the purified antigen, ganglioside GM3, was tested. Ganglioside GM3 includes a terminal sugar having NeuAc $\alpha$ 2-3 Galactose residue. The three assay systems were: IA inhibition, cell-ELISA inhibition, and GM3-ELISA inhibition. Of the 40 antibodies tested, seven inhibited L612 binding to an antigen positive target melanoma cell line, (UCLASO-M12), and to GM3 greater than 50% in the assays, while 12 others had weak or no inhibitory activity.

Of the seven inhibitory anti-ids, one identified as 4C10 was selected for cloning as the preferred beta-type anti-id for use in treating tumors. From the non-inhibitory group the anti-id identified as 18C6 was selected for cloning as the preferred alpha-type anti-id for use in immunodiagnostic assays. Both anti-ids, 4C10 and 18C6, were tested with isotype antigloboulins and found to be of the IgG1 class and contain kappa light chains.

The 4C10 and 18C6 cloned hybridoma cell lines were grown in FCS-containing RPMI 1640 medium and secreted 5-10 ug/ml of antibody into culture supernatants. Titers of the anti-ids in these culture supernatants against L612 by ELISA ranged between 1:200 to 1:1000/$10^6$ hybridoma. Anti-id 18C6 demonstrated low binding inhibition of HuMAb L612 to target cells in the IA assay (0%) and to ganglioside GM3 in ELISA (0%) whereas 4C10 at the same antibody concentration showed strong inhibition in both the ELISA assay (100%) and the IA assay (100%). As a control assay, 4C10 and 18C6 failed to inhibit the binding of an unrelated antigen system, HuMAb L72, to M14 target cells, or to GD2 antigen. The lack of binding inhibition of 18C6 indicates a binding location on L612 outside the GM3 antigen combining site, and the specific binding inhibition of 4C10 indicates its binding location to be within or near the antigen combining site.

The hybridoma cell lines which secrete the 4C10 and 18C6 monoclonal anti-ids are, as previously mentioned, being maintained at the Divsion of Surgical Oncology at the University of California at Los Angeles School of Medicine. The 4C10 hybridoma cell line has been deposited at the American Type Culture Collection under ATCC accession number HB10722. The 18C6 hybridoma cell line has also been deposited under ATCC accession number HB10723.

The 4C10 anti-id and other beta-type anti-ids in accordance with the present invention can be used alone or in combination with other agents to treat tumors. They are preferred for use in treating melanoma tumors. These beta-type anti-ids may also be used as an immunomodulator to enhance anti-cancer immunity, suppress organ transplant rejection and suppress autoimmune disease.

The beta-anti-ids of the present invention may be administered by any of the conventional procedures used to introduce antibodies into patients. These procedures include subcutaneous, intravenous or intratumor injection. The beta-type anti-ids are preferrably conjugated with KLH and emulsified in a suitable carrier typically used for administration of antibodies. The particular doses used for the beta-type anti-ids will vary depending upon the tumor being treated and numerous other factors. The dosage levels are established by the known techniques and principles generally recognized and utilized in treating patients with antigen immunization agents or monoclonal antibodies.

The immunogenic usefulness of the beta-type anti-ids was demonstrated as follows:

Five syngeneic Balb/c mice were immunized with purified 4C10-KLH. As controls, four mice were immunized with mouse IgG1-KLH and one mouse with KLH alone. The immunized sera were monitored by ELISA using purified GM3 as the antigen source and by the IA assay using the antigen positive M12 melanoma cell line. In the ELISA, peroxidase conjugated goat anti-mouse IgM+IgG (Boeringer Mannheim) was used as a second antibody.

Measurable antibody (AB3) was produced in three of the five immunizations with 100 ug 4C10-KLH. The immunized sera bound to GM3 but not to CDH (asialo-GM3). Sera from the control mice immunized with IgG-KLH or KLH alone gave no response to either glycolipid. In further analysis to determine the Ig class of the AB3 (ELISA and TLC immunostaining), the majority of the reactivity was identified as IgM.

In order to exclude the species specific natural antibodies that might react to M12 cells in the IA assay, the immunized murine sera were pre-absorbed by human red blood cells at 4° C. overnight. An IA score of 4+ was obtained at 1:10 dilution of the absorbed sera. Control sera gave no reactivity even at 1:2 dilution. To confirm that the positive reactivity was directed against GM3 antigen on the cell surface, IA inhibition was performed using GM3 (10 ug), CDH (10 ug), 4C10 (10 ug) and unrelated IgG1 (10 ug) purified from Balb/c hybridoma ascites. While reactivity was completely inhibited by GM3 or purified 4C10, no inhibition was obtained with CDH or unrelated IgG1.

The above example demonstrates that beta-type anti-ids in accordance with the present invention produce AB3 anti-bodies which are immunoreactive with melanoma tumors. Accordingly, these beta-type anti-ids are expected to be effective as an immunization agent in the treatment of melanoma.

The alpha-type anti-ids produced in accordance with the present invention are well-suited for use in immunodiagnostic procedures such as a three-step cell-ELISA procedure and a three step immunoperoxidase staining of tumor tissue sections. Examples of practice are as follows:

Three-Step Cell-ELISA

Viable M12 cells ($1 \times 10^5$) were plated onto a U-bottom 960well microtiter plate (Immulon-1, Dynatec) after pre-blocking with 1% BSA-PBS. 50 ul of L612 (100 ug/ml) were added and incubated for 1 hour at room temperature. After washing the mixture to remove unbound HuMAb L612, the cells were incubated with murine monoclonal anti-id 18C6 (100 ug/ml) for 1 hour at room temperature. After washing, 50 ul of peroxidase-conjugated goat anti-mouse IgG antibody (1/10,000 diluted) (Jackson Immuno Research) were added and the plate was incubated for 30 minutes. After washing with PBS solution, the substrate for peroxidase was added and binding activity was determined as a function of absorbance at 490 nm with a $V_{max}$ kinetic microplate reader.

When the antigen combining sites of L612 are occupied by GM3 expressed on tumor cells, the cell bound L612 should have reduced its binding activity to anti-id beta, yet still retain full binding activity to anti-id alpha. The above-described procedure confirmed this process using cultured M12 melanoma cells which express a high density of the corresponding antigen.

The above-described cell binding assay represents a modified form of the ELISA technique. Several control assays were included to establish the specificity of the positive reaction. Control anti-ganglioside HuMAbs included L55 (IgM anti-GM2) and L72 (IgM anti-GD2), both of which exhibit strong binding ability to the GM2 and GD2 rich M14 melanoma cell line (26, 27). The anti-id 18C6 reacted strongly to M12 cells after pre-incubation with HuMaB L6I2, but did not react to M14 cells that were pre-incubated with L55 or L72 HuMAb. The peroxidase-conjugated anti-mouse Ig also failed to react with M12 cells in other controls including murine anti-id alone, L612, or L612 plus (anti-id beta).

The cell-ELISA assay was then applied to several other human tumor cell lines. A two-step cell binding assay (HuMAb +peroxidase-conjugated anti-human IgM) was compared with the three-step cell-binding assay to evaluate the validity of the three-step assay. The three-step assay had parallel reactivity with the two-step assay and was slightly more sensitive in almost every cell line. This data indicates that the ELISA absorbancy value of the three-step assay accurately reflects differences in the density of cell surface GM3 antigens and correlates closely with the two-step in vitro assays.

Three-Step Immunoperoxidase Staining of Tissue Sections

Tissue sections 4 um thick were cut from tissues freshly frozen in OTC compound and immediately fixed in cold formaldehyde buffer (12 g Tris buffer, 9 g sodium chloride, 40 ml 37% formaldehyde, pH 7.4) and air dried. Slides were dipped in Tris buffer for five minutes then treated with 3% hydrogen peroxide for 10 minutes to quench endogenous peroxidase activity.

After washing in running water for five minutes, sections were overlaid with 5% normal human serum for 20 minutes. HuMAb L612 (10 ug IgM in 200 ul) was then applied and incubated for 45 minutes. The slides were washed in Tris buffer for 5 minutes, the purified anti-id 18C6 (10 ug IgG1 in 200 ul) was applied and incubated for 30 minutes.

After washing the slides again, the third antibody, a biotinylated goat anti-mouse IgG (Vector Laboratories, Burlingame, Calif.) at 1/100 dilution was applied and incubated for 25 minutes. Proxidase-conjugated streptavidin (1/1000 dilution) (Zymed Laboratories, San Francisco) was added after washing and incubated for 20 minutes. After washing, the slides were immersed in substrate solution containing 6 ml amino-ethyl carbazole, 50 ml of 0.02 M sodium acetate buffer (pH 5.1), and 0.4 ml of freshly prepared 3% hydrogen oxide for 5 minutes. The slides were washed once more in tap water, counterstained with hematoxoylin, and cover-slips applied to the stained sections using glycerol-gelatin.

The immunoperoxidase three-step assay described above was applied to surgically biopsied tumor tissues that had been snap frozen. HuMAb L612 was found to react with 100% of nevus tissue (10/10), 100% of melanoma (14/14), 40% of lung caroinoma (2/5), and 33% of breast carcinoma (2/6) and 1 of one colon carcinoma. Positive reactivity was not seen in sarcomas (0/2) tested, nor in the normal skin tissues examined (0/3). Non-cancerous portions of antigen-positive tumor sections and a normal skin tissue were clearly negative. None of the tumor tissues were positive in the absence of L612. Specificity was further confirmed by an additional control experiment: positivie tissues were not stained when they were pre-treated with unrelated human monoclonal antibodies (L72 or L55 HuMAbs).

These above results show that murine anti-id alpha in accordance with the present invention is a sensitive and specific probe for use in detecting huMAbs bound to biopsied tumor tissues and to identify expression of ganglioside antigens on biopsied human tissues.

Having thus described exemplary embodiments of the present invention, it should be noted by those skilled in the art that the within disclosures are exemplary only and that various other alternatives, adaptations and modifications may be made within the scope of the present invention. For example, the anti-ids in accordance with the present invention may be used to make chimeric antibodies which are also useful in a variety of treatments or as diagnostic reagents. The anti-ids may also be used in other diagnostic procedures such as competitive binding assays. Accordingly, the present invention is not limited to the specific embodiments as illustrated herein, but is only limited by the following claims.

BIBLIOGRAPHY

1. Jerne NK. Towards a network theory of the immune system. Ann Immunol (Paris) 125C:373-389, 1974.
2. Dalgleish AG, Kennedy RC. Anti-idiotype antibodies as immunogens: idiotype-based vaccines. Vaccine 6:215-220, 1962.
3. Sikorska HM. Therapeutic applications of anti-idiotypic antibodies. J Biol Res Mod 7:327-358, 1988.
4. Livingston PO, Natoli EJ, Calves MJ, Stockert E, Oettgen HF, Old LJ. Vaccines containing purified GM2 ganglioside elicit GM2 antibodies in melanoma patients. Proc Natl Acad Sci USA 84:2911-2915, 1987.
5. Livingston PO. Experimental and clinical studies with active specific immunotherapy. In "Immunity to Cancer II." Eds MS Mitchell, Pub Alan L Liss, Inc, NY.
6. Herlyn D, Wettendorff M, Schmoll E. Anti-idiotype immunization of cancer patients: modulation of immune response. Proc Natl Acad Sci 84:8055-8059, 1987.
7. Bhattacharya-Chatterjee M, Pride MW, Seon BK, Kohler H. Idiotype vaccines against human T-cell acute lymphoblastic leukemia. I. Generation and characterization of biologically active monoclonal anti-idiotypes. J Immunol 139:1354-1360, 1987.
8. Viale G, Grassi F, Pelagi M, Alzani R, Menard S, Miotti S, Buffa R, Gina A, Siccardi AG. Anti-human tumor antibodies induced in mice and rabbits by "internal image" anti-idiotype monoclonal immunoglobulins. J Immunol 139:4250-4255, 1987.
9. Chen H, Mittelman A, Yamada M. Association of restricted specificity of anti-anti-idiotypic antibodies with prolonged survival of melanoma patients. Proc Amer Assoc Clin Oncol 8:A1125, 1989.

10. Kahn M, Hellstrom I, Estin CD, Hellstrom KE. Monoclonal anti-idiotypic antibodies related to the p97 melanoma antigen. Cancer Res 49:3157–3162, 1989.
11. Barth A, Waibel R, Stahei RA. Monoclonal anti-idiotypic antibody mimicking a tumor-associated sialoglycoprotein antigen induces humoral immune response against human small cell lung carcinoma. Int J Cancer 43:896–900, 1989.
12. Irie RF, Matsuki T, Morton DL. Human monoclonal antibody to ganglioside GM2 for melanoma treatment. Lancet 1:786–787, 1989.
13. Tsuchida T, Saxton RE, Morton DL, Irie RF. Gangliosides of human melanoma II. Cancer, 623:1166–1174, 1989.
14. Ravindranath MH, Morton DL, Irie RF. An epitope common to ganglioside 0-acetyl AD3 recognized by antibodies in melanoma patients after active specific immunotherapy. Cancer Res 49:3691–3897, 1989.
15. Hoon DBS, Ando I, Sviland G, Tsuchida T, Okun E, Morton DL, Irie RF. Ganglioside GM2 expression on human melanoma cells correlates with sensitivity to lymphokine-activated killer cells. Int J Cancer 43:857–862, 1989.
16. Hoon DBS, Irie RF, Cochran AJ. Gangliosides from human melanoma immodulate response of T-cells to interleukin-2. Cell Immunol 111:410–419, 1988.
17. Ravindranath MH, Paulson JC, Irie RF. Human melanoma antigen 0-acetylated ganglioside GD3 is recognized by cancer autennarius lectin.1 J Biol Chem 263:2079–2086, 1988.
18. Tsuchida T, Ravindranath MH, Saxton RE, Irie RF. Gangliosides of human melanoma Altered expression in vivo and in vitro. Cancer Res 47:1278–1281, 1987.
19. Tai T, Sze LL, Kawashima I, Saxton RE, Irie RF. Monoclonal antibody detects monosialoganglioside having sialic acid 2-3 Galactosyl residue. J Biol Chem 262:6803–6807, 1987.
20. Ando I, Hoon DSB, Suzuki Y, Saxton RE, Golub SH, Irie RF. Ganglioside GM2 on the K56 cell line is recognized as a target structure by human natural killer cells. Int J Cancer 40:12–17, 1987.
21. Tsuchida T, Saxton RE, Irie RF. Gangliosides of human melanoma: GM2 and tumorigenicity. J Natl Cancer Inst 78:55–60, 1987.
22. Tsuchida T, Saxton RE, Morton DL, Irie RF. Gangliosides of human melanoma. J Natl Cancer Inst 78:45–54, 1987.
23. Irie RF, Morton DL. Regression of cutaneous metastatic melanoma by intralesional injection with human monoclonal antibody to ganglioside GD2. Proc Natl Acad Sci 83:8694–8698, 1986.
24. Katano M, Irie RF. Suppressed growth of human melanoma in nude mice by human monoclonal antibody to ganglioside GD2. Immunology Letters 8:169–174, 1984.
25. Katano M, Saxton RE, Irie RF. Human monoclonal antibody to tumor-associated ganglioside GD2. J Clin Lab Immunol 15:119–126, 1984.
26. Tai T, Paulson JC, Cahan LD, Irie RF. Ganglioside GM2 as a human tumor antigen (OFA-I-1). Proc Natl Acad Sci, USA 80:5392–5396, 1983.
27. Cahan LD, Irie RF, Singh R, Cassidenti A, Paulson JC. Identification of human neuroectodermal tumor antigen (OFA-I-1) as ganglioside GD2. Proc Natl Acad Sci 79:7629–7633, 1982.
28. Tai T, Cahan LD, Tsuchida T, Saxton RE, Irie RF, Morton DL. Immunogenicity of melanoma-associated gangliosides in cancer patients. Int J Cancer 35:607–612, 1985.
29. Irie RF, Sze Ll, Saxton RE. Human antibody to OFA-I, tumor antigen produced in vitro by EBV-transformed human B-lymphoblastoic cell lines. Proc Natl Acad Sci 79:5666–5670, 1982.
30. Yano T, Yasumoto K, Nagashima A, Murakami H, Hashizume S and Nomoto K (1988) Immunohistological characterization of human monoclonal antibody against lung cancer. J Surg Oncol. 39, 108.

What is claimed is:

1. A murine monoclonal anti-idiotype antibody raised against a human monoclonal anti-ganglioside antibody identified as L612 under ATCC accession number CRL10724 said anti-idiotype antibody including an antigenic determinant that mimics a sialic acid galactose residue of gangliosides present on tumors wherein said anti-idiotype antibody is an alpha-type anti-idiotype antibody produced by a hybridoma which is identified as 18C6 and which is deposited at the American Type Culture Collection under ATCC accession number HB10723.

2. A hybridoma which is identified as 18C6 and which is deposited at the American Type Culture Collection under ATCC accession number HB10723.

3. A method for detecting the presence of human monoclonal antibody bound to human tumor tissue comprising the steps of treating said human tumor tissue with an immunoreactive amount of anti-idiotype antibody for a sufficient time to allow said anti-idiotype antibody to bind to human monoclonal antibody; and detecting the presence of any anti-idiotype antibody which becomes bound to said human monoclonal antibody, wherein said anti-idiotype antibody is an alpha-type anti-idiotype antibody produced by a hybridoma which is identified as 18C6 and which is deposited at the American Type Culture Collection under ATCC accession number HB10723.

* * * * *